United States Patent
Sgro (10) Patent No.: US 7,488,335 B2
(45) Date of Patent: Feb. 10, 2009

(54) DEVICE FOR LIGATING AN ANATOMICAL STRUCTURE

(75) Inventor: Jean-Claude Sgro, Dijon (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 10/546,800

(22) PCT Filed: Feb. 23, 2004

(86) PCT No.: PCT/FR2004/000403

§ 371 (c)(1),
(2), (4) Date: Mar. 23, 2006

(87) PCT Pub. No.: WO2004/075762

PCT Pub. Date: Sep. 10, 2004

(65) Prior Publication Data

US 2006/0264987 A1 Nov. 23, 2006

(30) Foreign Application Priority Data

Feb. 24, 2003 (FR) .................................. 03 02216

(51) Int. Cl.
*A61B 17/04* (2006.01)
*A61B 17/12* (2006.01)
(52) U.S. Cl. ...................................... 606/144; 606/148
(58) Field of Classification Search ......... 606/139–140, 606/144, 157, 148, 149, 145, 141, 150; 600/29–30, 600/37; 433/15, 18
See application file for complete search history.

(56) References Cited

U.S. PATENT DOCUMENTS

| 4,592,355 | A | | 6/1986 | Antebi |
| 5,383,882 | A | * | 1/1995 | Buess et al. .................. 606/157 |
| 5,447,512 | A | * | 9/1995 | Wilson et al. ................ 606/139 |
| 5,609,599 | A | | 3/1997 | Levin |
| 5,749,879 | A | * | 5/1998 | Middleman et al. ......... 606/139 |
| 5,766,189 | A | | 6/1998 | Matsuno |
| 5,782,839 | A | | 7/1998 | Hart et al. |
| 6,261,303 | B1 | | 7/2001 | Mayenberger |

FOREIGN PATENT DOCUMENTS

| DE | 1 957 855 | | 5/1971 |
| EP | 0 537 955 A2 | * | 4/1993 |
| EP | 0 637 432 A1 | | 2/1995 |
| WO | WO 01/34038 A2 | | 5/2001 |

* cited by examiner

*Primary Examiner*—Darwin P Erezo
*Assistant Examiner*—Lindsey Bachman
(74) *Attorney, Agent, or Firm*—Kenyon & Kenyon LLP (57) ABSTRACT

A device for ligating an oblong anatomical structure having a ligature element. A proximal portion of the ligature element may have a keeper and the distal portion may have a barb which is slidably received in the keeper. The device may further include an applicator for putting the ligature element in place, a rectilinear metal rod which extends in the tube and which, at its distal end has a spring blade, and a sheath having a radial outer duct in which the spring blade is received, and a radial inner guide groove in which the ligature element is received.

5 Claims, 10 Drawing Sheets

DEVICE FOR LIGATING AN ANATOMICAL STRUCTURE

This is a 371 national phase application of PCT/FR04/00403 filed 23 Feb. 2004, claiming priority to French Patent Application No. 0302216 filed 24 Feb. 2003, the contents of which are incorporated herein by reference.

BACKGROUND OF THE INVENTION

The invention relates to a device for ligating an anatomical structure.

The device of the invention relates to the field of surgical equipment making it possible to perform surgery, in particular in small spaces, especially under celioscopy. That minimally-invasive technique involving the use of fine, cylindrical instruments passed through the abdominal wall without using a large opening makes it impossible to use the fingers or the hand.

For example, for surgical resection of the vermiform (or cecal) appendix, the operation is relatively simple when it is performed via conventional open surgery; it is necessary to control and then cut the vessels that supply the appendix and that are included in an anatomical fold known as the "mesoappendix". Then the junction between the base of the appendix and the cecum, which is the lower portion of the right colon must be ligated. Finally, the appendix must be cut off just above the ligature. The celioscopic technique also involves these operating stages, but it represents a more difficult technique. The difficulty raised by the section of the mesoappendix is currently solved, for this type of surgery, either by using an electric knife, or by using metal clips. But the use of electrical power is dangerous, and should be avoided. As for using metal clips, that requires equipment that is complex, costly, and sometimes of inappropriate size. Ligating the appendicular base, which, in theory, is relatively easy, is often more difficult than expected. Pre-mounted slip knots are available but they are flexible, so passing them around the appendix requires great care, and they must be tightened with precaution so as not to cut off the appendix completely, but sufficiently tightly so that the knot does not come undone and so that the tissue does not slip.

The state of the art is illustrated by WO 01/34038, U.S. Pat. Nos. 5,476,206 and 5,433,721.

WO 01/34038 describes an instrument making it possible to take hold of an appendicular stump and to slide an elastic band over it. The same technique is used for the mesoappendix. That assumes that the appendix is thin enough and flexible enough to be received in the instrument, and that the mesoappendix is thin enough and flexible enough, or that the base of the appendix and the mesoappendix have already been cut off.

In certain special cases when the appendix is extremely reworked or has increased in volume, it can be necessary to use more complex and costly instruments such as those described in Patents U.S. Pat. Nos. 5,476,206 and 5,433,721. Those instruments make it possible to staple two rows of staples and to cut between the two rows. Admittedly, the result is satisfactory but such instruments cannot be used systematically because they require accesses that are larger than those usually formed for surgical resection of the appendix, and they are costly. The accesses required for such instruments have diameters lying in the range 10 millimeters (mm) to 12 mm instead of 5 mm;

Currently, no other equipment exists for performing the various surgical stages.

SUMMARY OF THE INVENTION

An object of the invention is to mitigate this lack. Individual devices for use once only can be suitable, because two clips can suffice for treating simple lesions, an appendectomy, or an isolated blood vessel ligature.

The invention thus provides a device for ligating an oblong anatomical structure such as a vermiform appendix, a mesoappendix, or a blood vessel, the device comprising a clip and an applicator, forming a unit that is dissociated only at the end of ligating, it being necessary for the device to be manipulated with one hand only for the purposes of hooking onto the anatomical structure, of binding it, and optionally of cutting it off.

According to the invention, the device is characterized by the fact that it comprises:

firstly, a ligature element having a first branch and a second branch, each of which has a proximal end, a distal end, an inside face and an outside face, a flexible thin strip forming a hinge and interconnecting the distal ends of said two branches, and means for coupling together at least the proximal portions of said two branches, said two branches co-operating, once they have been coupled together, to form between them a transverse channel clamping around a portion of said anatomical structure; and secondly, an applicator for putting in place said ligature element, said applicator comprising:

a cylindrical body having a distal end and a proximal end;

a holder for receiving said ligature element, said holder having a side wall organized at the distal end of said body and against which the outside face of the first branch of said ligature element is in abutment, in particular while it is being transported;

means for moving the second branch away from the first branch for the purpose of hooking onto the anatomical structure to be ligated;

means for moving the second branch towards the first branch in order to couple said two branches together; and a slide making it possible to act on the means for moving the second branch away from or towards the first branch.

According to an advantageous characteristic, the slide is mounted to move at least along the side wall of said holder, said slide including the means for moving the second branch away from or towards the first branch, and being suitable for being moved axially by a drive member disposed at the proximal end of said body and connected to said slide by a rod mounted to slide in said body.

In a first embodiment of the ligature element of the embodiment the two branches of the ligature element are rectilinear and rigid, and the means for coupling the two branches together comprise male snap-fastening elements and female snap-fastening elements provided on the inside faces of said two branches.

Advantageously, the female snap-fastening elements comprise at least one longitudinal groove having reentrant edges and opening out in the inside face of one of the branches, and the male snap-fastening elements comprise at least one cylindrical wall formed on the inside face of the other branch and suitable for being inserted by force into the corresponding groove.

According to a particular characteristic, the inside face of each of the two branches is provided with a transverse recess, said recesses co-operating, after the male elements have been snap-fastened into the female elements, to form said transverse channel.

With this first embodiment of the ligature element, the slide is in the form of a trough having two parallel axial lips, said lips having, at one end, a pair of facing projections designed to slide in longitudinal guide groves provided in the outside face of at least one of the two branches of said ligature element and in the outside face of the side wall of the holder, the outside faces of said branches having, in said guide grooves, at least one pair of protuberances which, by co-operating with the pair of projections of said slide, while said slide is moving axially, cause the two branches of said ligature element to clamp together and cause the fastening means to snap-fasten together.

In order to move the two branches of the ligature element apart positively, said two branches are extended beyond the hinge, and the groove of the second branch has a second protuberance in the corresponding extension, which second protuberance co-operates with a projection on the slide while said slide is moving axially to cause the second branch to move away from the first branch.

According to another advantageous characteristic, the edge of the trough that extends between the pair of projections is disposed substantially in a slanting plane and is beveled in order to serve as a tool for cutting off the anatomical structure clamped by said ligature element, by the slide moving axially.

In a second embodiment of the ligature element, the two branches of the ligature element are resiliently deformable. On its inside face and in the vicinity of its proximal end, the first branch has a keeper having a proximal end and a distal end, and, in whose orifice the proximal portion of the second branch inserted via the distal end is slidably received, and, at its proximal end, the second branch has locking means co-operating with said keeper.

The holder is then further provided with a leaf spring or spring blade connected to the distal end of the side wall of said holder via a flexible hoop, said spring blade having a convex surface facing said side wall, which convex surface is in abutment against the outside face of the second branch of said ligature element, and the slide is constituted by a ring through which said side wall and said spring blade pass, axial movement of said ring along said side wall causing said spring blade to move towards or away from said side wall.

In a variant of the second embodiment of the ligature element, in its wall distant from the inside face of the first branch, the keeper is provided with a longitudinal slot open at both of its ends, and, extending its proximal end and in alignment with it, the second branch has a tongue suitable for being inserted into said keeper by sliding through said slot, said tongue having a length longer than the length of the keeper and having graspable means at its free end.

The applicator is then provided with a receptacle for receiving said graspable means, said receptacle being mounted to move axially and being connected to a second drive member provided at the proximal end of the body via a second rod mounted to slide in said body.

In a third embodiment of the ligature element, said ligature element is in the form of a flexible strip having a proximal portion and a distal portion, the proximal portion having a keeper, and the distal portion having a barb at its free end and being suitable for being slidably received in said keeper after it has been inserted via the distal end of the keeper after traction has been exerted on the barb.

The applicator for putting said ligature element in place comprises:

a cylindrical tube having a distal end and a proximal end;
a rectilinear metal rod which extends in said tube and which, at its distal end has a spring blade which, in the absence of stress, forms substantially a circle extending from said rod and whose diameter lies in the range five times the inside diameter of said tube to twelve times said inside diameter, said blade being suitable for being received in said tube in the deployed state and for resuming its circular shape when it is brought out via the distal end of said tube;
means for acting, at least while it is being transported, to retains said ligature element on the inside face of said spring blade, the keeper being disposed at the distal portion of said rod; and
a wire guide or feedthrough passing through said keeper and, at the front of the distal end of said keeper, forming an eye into which the distal end of the ligature element is inserted when the spring blade forms a circle, so that traction exerted on said feedthrough causes said eye to be hooked by the barb, causes the distal portion of the ligature element to be inserted into said keeper, and causes said ligature element to be tightened.

Advantageously, the means for retaining the ligature element comprise a sheath made of a flexible material and having a radially outer duct in which at least the spring blade is received, and a radially inner guide groove in which the ligature element is received at least in part, said guide groove being defined by two lips retaining the longitudinal edges of said ligature element and being suitable for moving apart to release said ligature element while it is being tightened.

In an advantageous variant, the keeper is constituted by two orifices provided in the proximal portion of the ligature element and via which the feedthrough passes.

Preferably, the distal end of the tube is also provided with cutting means for cutting off the distal end of the ligature element after said ligature element has been tightened.

The cutting means are formed by the sharp edges of a notch provided at the distal end of the tube.

BRIEF DESCRIPTION OF THE DRAWINGS

Other advantages and characteristics of the invention appear on reading the following description given with reference to the accompanying drawings, in which.

DETAILED DESCRIPTION

FIGS. 1 to 10 show a ligature element 1 for ligating, in particular, an oblong anatomical structure. The ligature element has two rigid branches 2a, 2b, each of which has a proximal end 4a, 4b, a distal end 5a, 5b, an inside face 6a, 6b, and an outside face 7a, 7b, the index "a" of the references 4 to 7 relating to the first branch 2a, and the index b of the references 4 to 7 relating to the second branch. A flexible thin strip 10 interconnects the distal ends 5a, 5b of the two branches 2a and 2b. The ligature element 1 is preferably made by molding or by cutting out and of a suitable material complying with medical requirements, and in particular of a resorbable material, and the flexible thin strip 10 is chosen such that, at rest, the two branches 2a and 2b form an acute angle.

Thus, as can be seen clearly in FIGS. 1 and 2, which show ligature elements 1 serving to be put in place by an applicator described below, the inside face 6a, 6b of each of the branches 2a and 2b is provided with a respective transverse recess 11a, 11b, the recesses forming a transverse channel 12 serving to clamp around a portion of the anatomical structure.

Figure 5:
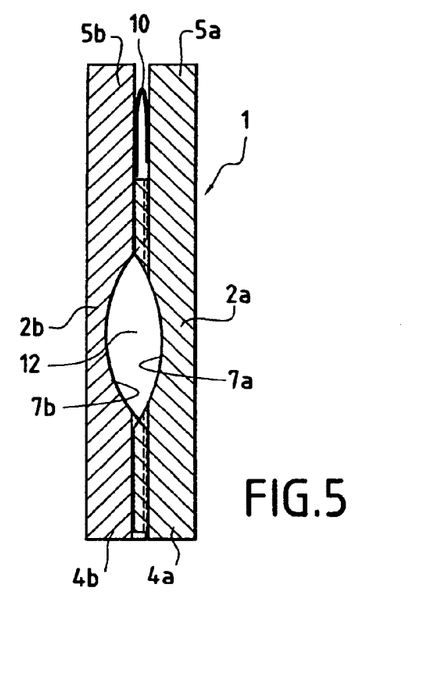
FIG. 5 is a plan view of the ligature element of FIG. 4 in the locked position.

The inside face 6b of the second branch 2b is provided with a longitudinal groove 13 that is designed to receive, by force-fitting, a cylindrical wall 14 provided on the inside face 6a of the first branch 2a. The groove 13 is formed such that its edges are reentrant and such that, on the inside surface 6b, it has lips 15a, 15b which deform elastically when the cylindrical wall 14 is inserted between them, the insertion being obtained by bringing the two branches 2a, 2b towards each other and by exerting compression forces on them. The cylindrical wall 14 is connected to the first branch 2a by a wall 16 which has a thickness no greater than the distance between the two lips 15a and 15b. The diameter of the cylindrical wall 14 is no greater than the diameter of the groove 13. The dimensions of the groove 13 and of the cylindrical wall 14 are determined such that the cylindrical wall 14 can be inserted into the groove 13 by snap-fastening, the inside faces 6a and 6b of the two branches 2a and 2b then being adjoining, as can be seen in FIG. 5, in which the transverse channel 12 formed by the recesses 7a and 7b can be seen clearly.

Figure 1:
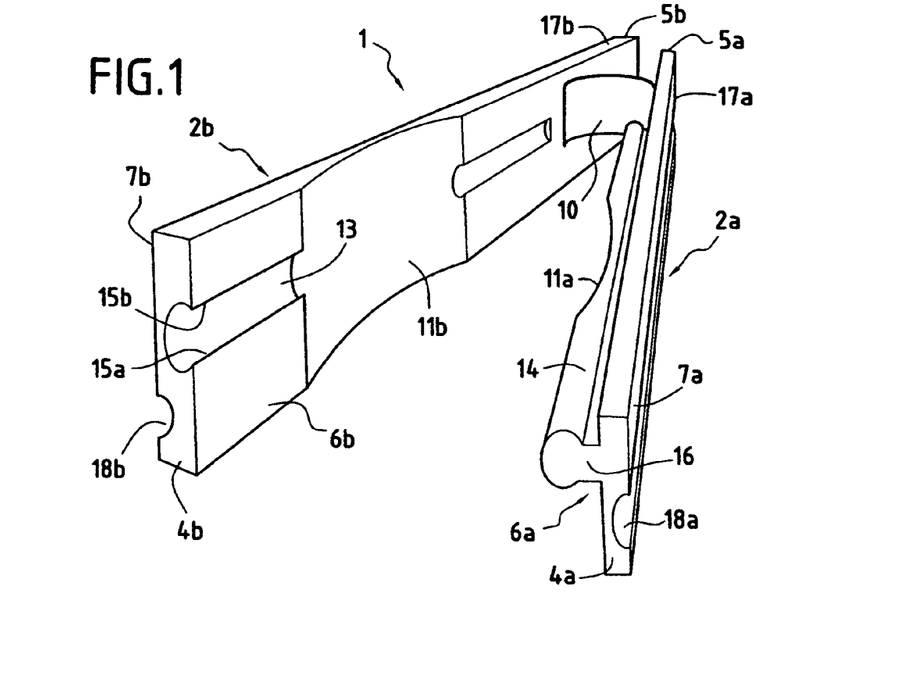
FIG. 1 is a perspective view of a first embodiment of a ligature element of the invention.
Figure 2:
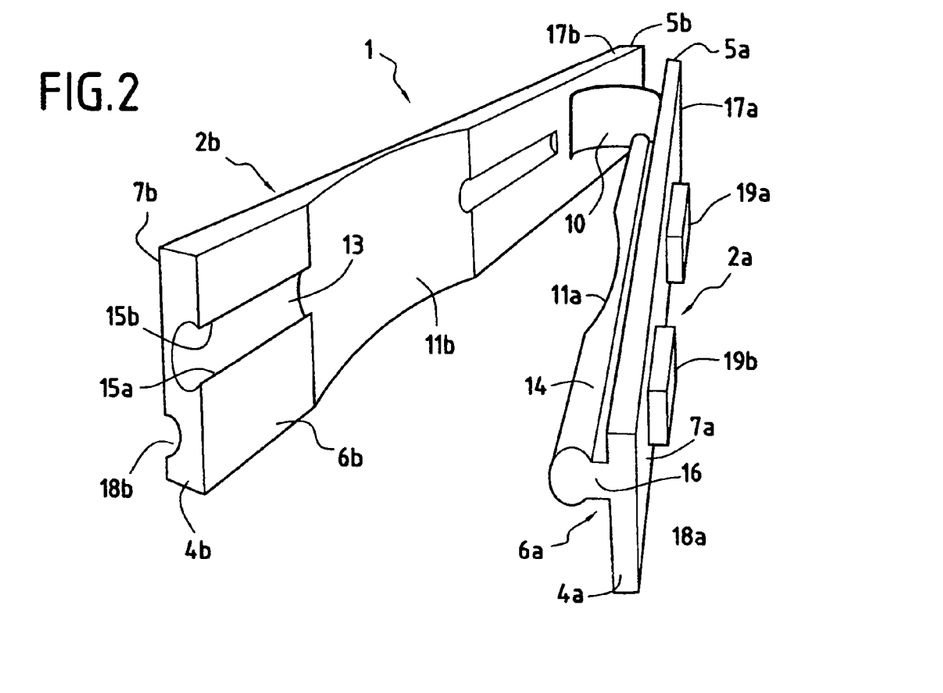
FIG. 2 shows a second variant of the first embodiment of the ligature element of the invention.

In FIGS. 1 and 2, it can be seen that, at their distal ends 5a and 5b, the branches 2a and 2b have end portions 17a and 17b that are situated beyond the connection of the flexible thin strip 10. The two end portions 17a and 17b serve to enable the two branches 2a and 2b to be moved apart when the applicator described below is put in place so that they can hook onto the anatomical structure.

As is shown in FIG. 1, the outside faces 7a and 7b of the two branches 2a and 2b are provided with longitudinal guide grooves 18a, 18b serving to guide a slide of the applicator. At least the longitudinal guide groove 18b in the branch 2b is provided with protuberances (not shown in FIGS. 1 and 2) which, by co-operating with a slide of the applicator, make it possible to bring the two branches 2a and 2b towards each other, and to insert the cylindrical wall 14 into the groove 13. Said protuberances are formed, in particular, close to the proximal end 4a, and optionally at other locations. In the guide groove 18b, the end portion 17b of the branch 2b also has a protuberance for moving the branch 2b away from the branch 2a.

FIG. 2 shows protuberances 19a on the outside face 7a of the branch 2a, for holding the ligature element 1 on the applicator, which protuberances also co-operate with the slide to compress the two branches 2a and 2b during the snap-fastening operation, as described in detail below.

Figure 3:
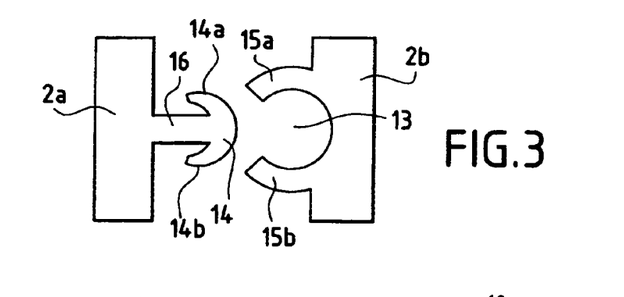
FIG. 3 shows a different shape for the male and female snap-fastening elements.

FIG. 3 shows a variant embodiment of the snap-fastening means. The groove 13 has resilient walls terminated by the lips 15a and 15b. The cylindrical wall 14 is also provided with flexible lips 14a and 14b that move towards each other as they pass between the lips 15a and 15b.

Figure 4:
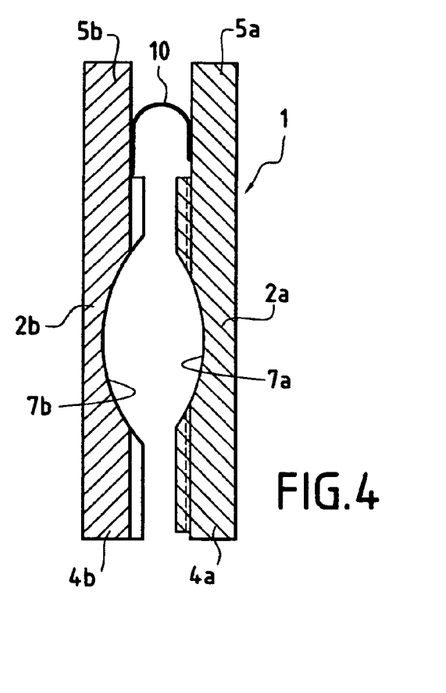
FIG. 4 is a plan view of the ligature element in a non-locked position.

FIG. 4 shows the ligature element in a transport position in which it is transported to its site of application. The two branches 2a and 2b are mutually parallel, but they are not secured together by the snap-fastening elements 13 and 14.

In this position, the ligature element 1 has a relatively small cross-sectional area.

FIG. 5 shows the ligature element 1 after the two branches 2a and 2b have been fastened together. The cross-section of the transverse channel 12 is adapted to match the cross-section of the anatomical structure on which the ligature element 7 is implanted.

Figure 6:
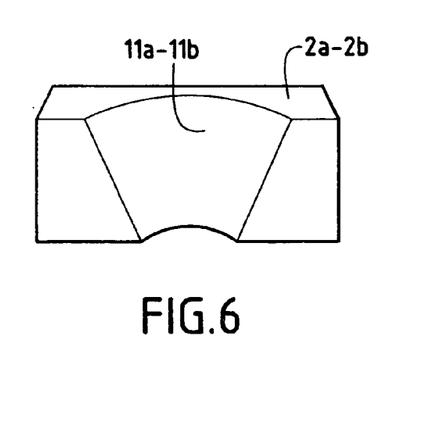
FIGS. 6 and 7 are views of the inside face of a branch of the ligature element, showing the variant embodiments of the recesses.
Figure 7:
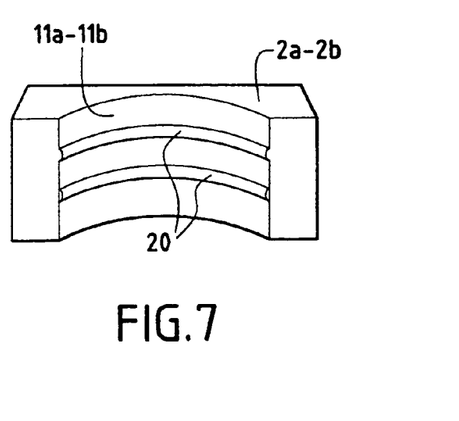

FIGS. 6 and 7 show two variant embodiments of the recesses 11a and 11b. FIG. 6 shows a recess having a shape that flares upwardly, while FIG. 7 shows a recess having parallel generator lines but having half-beads 20 in transverse planes, which half-beads enable the anatomical structure to be clamped firmly.

Figure 8:
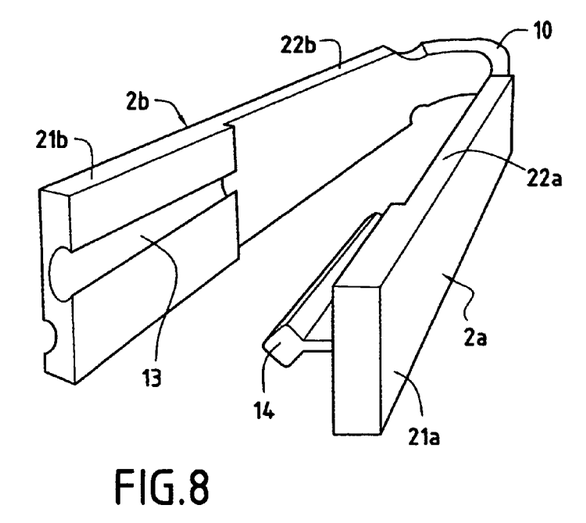
FIG. 8 shows a third variant of the first embodiment of the ligature element of the invention.
Figure 9:
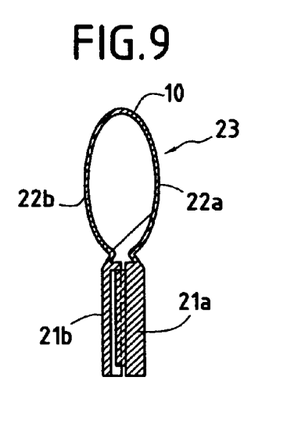
FIG. 9 is a plan view of the ligature element of FIG. 8 in the locked position.

FIGS. 8 and 9 show a ligature element 1 in which only the proximal portions 21a and 21b of the branches 2a and 2b are provided with snap-fastening means 13 and 14 such as the snap-fastening means described above, the other portions 22a, 22b of the branches 2a and 2b being thinner and being suitable for deforming elastically so as to co-operate with the hinge 10 to form a loop 23, after snap-fastening, as is shown in FIG. 9.

Figure 10:
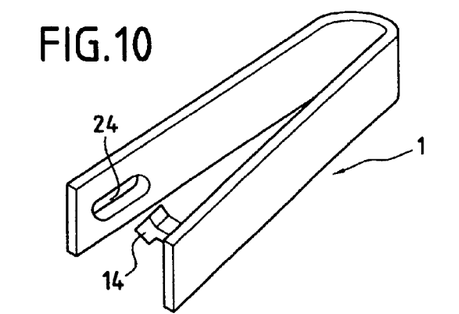
FIG. 10 shows a simplified fourth variant of the first embodiment of the ligature element of the invention.

FIG. 10 shows a simplified variant of the ligature element 1, in which the groove 13 is replaced with a window 24 through which the male snap-fastening element 14 is locked.

FIGS. 11 to 17 show, in detail, an applicator 30 for putting in place the ligature element 1 that is shown in FIGS. 1 and 2.

Figure 11:
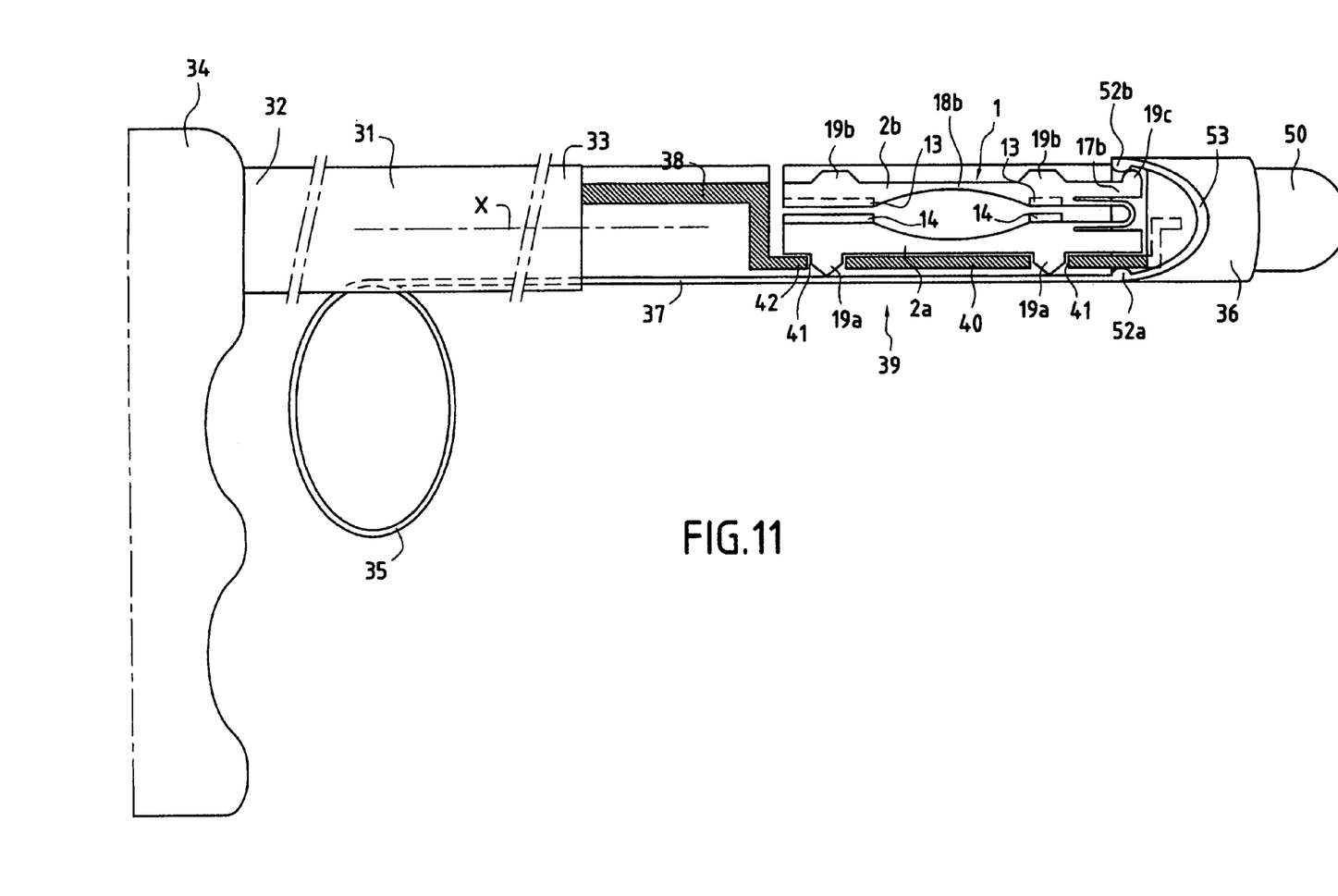
FIG. 11 shows an applicator that is particularly suitable for putting in place the ligature element shown in FIGS. 1 and 2.

The applicator 30 includes a cylindrical tube or body 31 which has a proximal end 32 and a distal end 33. The body 31 has a small diameter, e.g. 5 mm, and is designed to pass through a cannula disposed by means of a trocar through the wall of a patient.

The proximal end 32 of the body 31 is preferably equipped with a handle 34. Facing the handle, the body 31 is equipped with a drive member 35 mounted to move axially on the body 31 and connected to a slide 36 (described in more detail below) by a rod 37 mounted to slide in the body 31.

Figure 12:
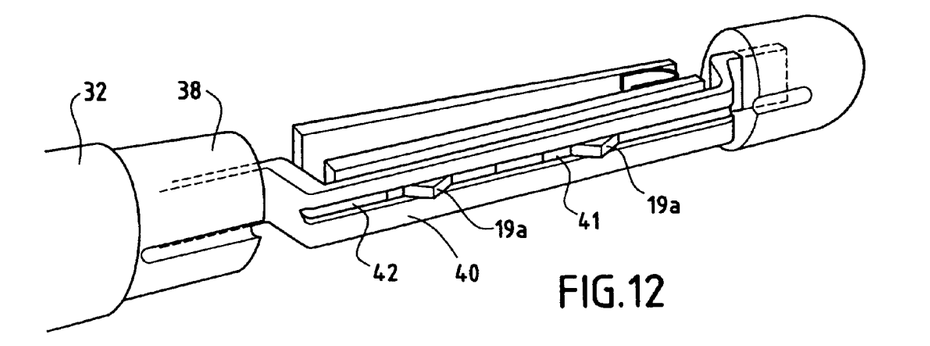
FIG. 12 is a perspective view of the distal end of the applicator of FIG. 11, without the slide.
Figure 13:
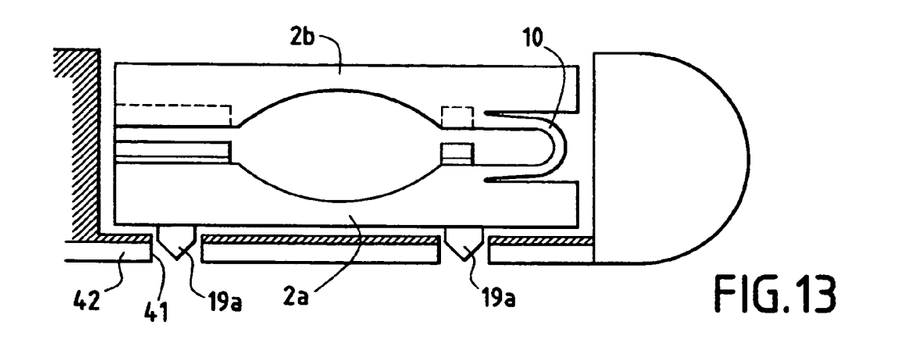
FIG. 13 is a section view on a transverse midplane of the distal end of the applicator without the slide.
Figure 14:
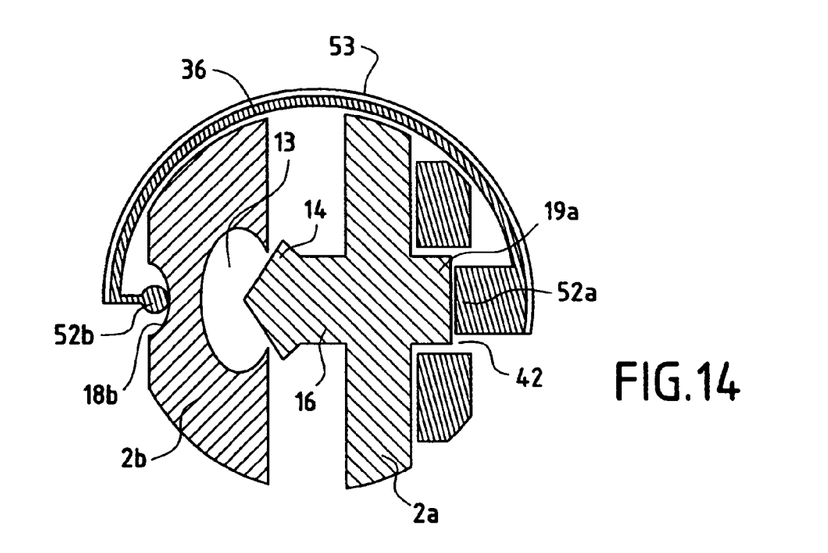
FIG. 14 is a section view on a plane perpendicular to the axis of the applicator of the distal end thereof, with the slide.

At its distal end 33, the body 31 has a smaller-diameter portion 38 that is suitable for receiving the slide 36. Said smaller-diameter portion 38 is extended by a holder 39 designed to receive a ligature element 1. The holder 39 is constituted essentially by a U-shaped plate which comprises a side or bottom wall 40 parallel to the axis X of the body 31 and against which the outside face of the first branch 2a of the ligature element 1 is retained by means of the protuberances 19a being received in windows 41 provided in the side wall 40, the windows themselves opening out into a longitudinal guide groove 42 provided in the outside face of the side wall 40. The protuberances 19a and 19b emerge into the guide groove 42.

As is shown in FIG. 11, in the guide groove 18b, the outside face of the second branch 2a also has two protuberances 19b opposite from the two protuberances 19a, each pair of protuberances 19a, 19b being positioned axially or longitudinally at a pair of snap-fastening means 13 and 14.

It can also be seen in this figure that the guide groove 18b has a third protuberance 19c at the free end of the extension 17b.

Reference 50 designates a foam end-piece disposed at the front end of the holder 39.

Figure 15:
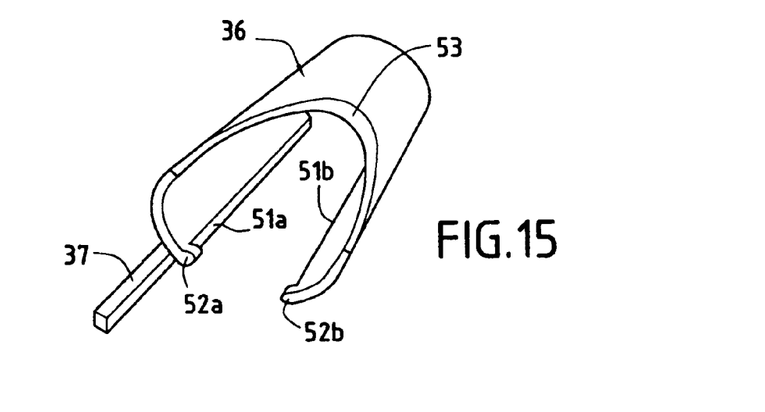
FIG. 15 is a perspective view of the slide.

The slide 36, shown in detail in FIG. 15, is in the form of a semi-cylindrical trough which has two longitudinal lips 51a, 51b. One of the ends of each of the lips has a projection 52a, 52b, the two projections 52a, 52b facing each other and being mounted to slide respectively in the guide groove 18b in the ligature element 1, and in the groove 42 in the side wall 40 of the holder 39.

The smaller-diameter portion 38 and the foam end-piece 50 also have guide grooves in alignment with the grooves 18b and 42.

As can also be seen in FIGS. 11 and 15, the edge 53 of the slide that extends between the two projections 52a and 52b is disposed in a slanting plane and is beveled in order to form a cutting tool for cutting off the anatomical structure after said structure has been ligated.

The above-described applicator 30 is used in the manner described below.

The ligature element 1 is disposed in the holder 39, the protuberances 19a and 19b being positioned in the windows 41 and the slide 36 being situated at the foam end-piece 50.

By moving the slide to a small extent towards the distal end 32 of the body 31, the projection 52b is caused to pass beyond the protuberance 19c, and it comes into position between the middle protuberance 19b and the protuberance 19c. The ligature element 1 is then held captive in the holder 39, in the transport position, and the applicator 30 is ready for use.

When the applicator 30 is inserted via the cannula into the body of the patient, it is necessary to open the ligature element 1 in order to hook onto the anatomical structure. For this purpose, the operator moves the drive member 35 manually towards the distal end 33. The slide moves axially, and the projection 52b presses against the protuberance 19c of the extension 17b of the second branch 2b, thereby moving the second branch 2b away from the first branch 2a which is still held against the side wall 40.

As soon as the operator has hooked onto the anatomical structure, said operator pulls the drive member 35 manually, the slide 36 moves axially towards the proximal end 32, and the projections 52a and 52b encounter the first pairs of protuberances 19a, 19b, thereby moving the distal portions of the branches 2a, 3b towards each other and causing a cylindrical wall 14 to be snap-fastened into the adjacent groove.

By continuing to apply traction to the drive member 35, the projections 52a and 52b are caused to come into contact with the protuberances 19a and 19b situated in the vicinities of the proximal ends 4a, 4b of the two branches 2a and 2b, and the proximal portions of the branches 2a and 2b are snap-fastened on going beyond said protuberances. The ligature element 1 is then in place. By continuing to move towards the proximal end 32, the beveled edge 53 of the slide 36 cuts off the anatomical structure above the resulting ligature.

When the slide 36 is positioned on the narrower portion 38 of the cylindrical body 31, the ligature element 1 is released, and the releasing is facilitated by the fact that the projection 52a has disengaged the protuberances 19a and 19b in part from the window 41 during the axial movement of the slide 36.

Figure 16:
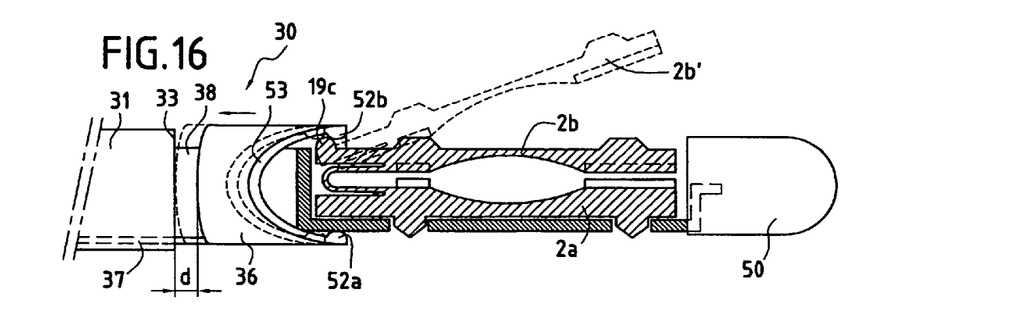
FIG. 16 shows a variant of the first embodiment of the applicator.

FIG. 16 shows a variant embodiment of the above-described applicator 30.

In this variant, the proximal ends 4a, 4b of the two branches 2a, 2b of the ligature element 1 are disposed in the vicinity of the foam end-piece 50, and the slide 36 has the projections 52a, 52b and the sharp edge 53 on the same side as the foam end-piece 50.

In FIG. 16, the position of the ligature element 1 and of the slide 36 when the applicator 30 is ready for use is shown in uninterrupted lines. The projection 52b is situated in front of the protuberance 19c. The slide 36 is at the narrow portion 38, its rear face being at a distance $\underline{d}$ from the distal end of the body 31. If the operator moves the slide 36 backwards by the distance $\underline{d}$, the projection 52b presses against the protuberance 19c. The branch 2b moves away from the branch 2a and takes up the position shown in dashed lines and referenced 2b'. Instead of forming a hook, the ligature element 1 is in the form of a clamp that the operator can position on the anatomical structure. Moving the slide 36 towards the foam end-piece 50 successively causes the two branches 2a and 2b to be closed and snap-fastened, and then the anatomical structure clamped in the transverse channel 12 of the ligature element 1 to be cut off.

It should be noted that, when the ligature element 1 is disposed in the holder 39 in the transport position, i.e. with the two branches 2a and 2b being mutually parallel but not locked, the cross-section of the assembly made up of the holder 39, of the ligature element 1, and of the slide 36 is no larger than the cross-section of the cylindrical body 31 in order to pass through the cannula of the trocar.

Figure 17:
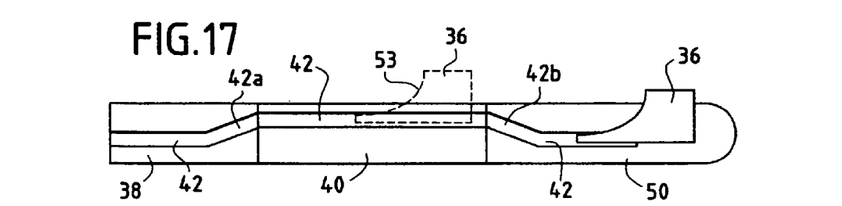
FIG. 17 shows a variant embodiment of the guide groove in the side wall of the holder for receiving the ligature element.

It should also be noted that the guide groove 42 provided in the outside face of the side wall 40 of the holder 39 over the narrower portion 38 and over the foam end-piece 50 can have segments 42a, 42b that are slanting in order to move the sharp edge 53 away from the ligature element 1 while the anatomical structure is being cut off, as shown in FIG. 17.

Figure 18:
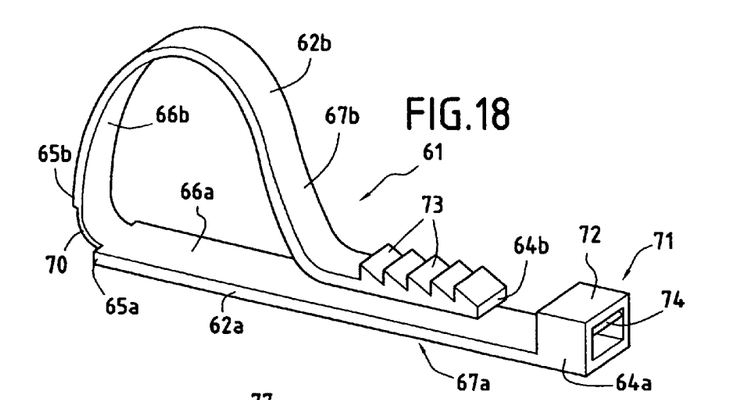
FIG. 18 is a perspective view of a second embodiment of the ligature element of the invention.

FIG. 18 shows a second embodiment of a ligature element 61 which has a first branch 62a that is semi-rigid and a second branch 62b that is also semi-rigid, each branch having a proximal end 64a, 64b, a distal end 65a, 65b, an inside face 66a, 66b and an outside face 67a, 67b. A flexible thin strip 70 interconnects the distal ends 65a, 65b of the two branches 62a and 62b. Said ligature element 61 is also preferably made by molding a suitable material, complying with medical requirements, in one piece or in a plurality of assemblable pieces.

On its inside face 66a, and in the immediate vicinity of its proximal end 64a, the first branch 62a has a keeper 71 of substantially rectangular cross-section, having a wall 72 remote from the inside face 66a.

On the outside face 67b of its proximal end, the second branch 62b has a plurality of transverse serrations 73. The cross-section of the duct 74 through the keeper 72 is determined such that the proximal portion of the second branch, inserted via the distal end of the duct 74, can slide under force or with slight friction in the duct 74, one of the serrations 73 then coming into abutment against the proximal end of the wall 72 in order to prevent the proximal portion from moving back again, thereby fastening the proximal portions of the two branches 62a and 62b together.

The serrations 73 can be disposed laterally over the proximal portion of the second branch 62b, or else they can be replaced merely with roughness, unevenness, stippling or studding, generating friction forces guaranteeing clamping.

Figure 21:
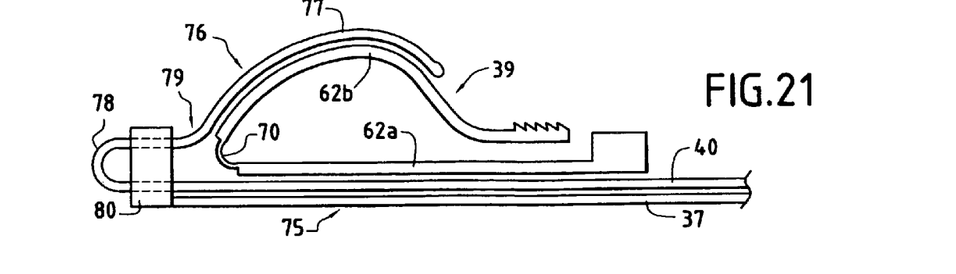
FIG. 21 shows the distal end of a specific applicator for putting in place the ligature element shown in FIG. 18.

FIG. 21 shows the distal end 75 of an applicator 30 for putting in place the second embodiment of the ligature element 61. This applicator 30 is substantially similar to the applicator described above and serving to put in place the first embodiment of the ligature element 1 of the invention. The only differences relate to the holder 39 for the ligature element 61 and the slide 36 connected to the drive member 35 by a rod 37 mounted to move axially.

The holder 39 has a side wall 40, and a spring blade 76 which, facing the side wall 40, has a convex surface 77 connected to the distal end of the side wall 40 via a hoop 78. The slide 36 is constituted by a ring 80 fastened to the distal end of the rod 37. The ring 80 is disposed in a plane perpendicular to the axis X of the applicator 30, and the side wall 40 and the spring blade 76 pass through it.

While the slide 76 is moving axially, the spring blade 76 and the side wall 40 slide in the bore of the ring 80.

The convex surface 77 is connected to the hoop 78 via a reverse-curvature connection zone or bend 79.

The ligature element 61 is disposed between the side wall 40 and the spring blade 76. The first branch 62a is in abutment against the side wall 40 and the second branch 62b is in abutment against the convex surface 77. The thin flexible strip 70 is disposed facing the hoop 78.

When the ring 80 is in its most distal position, the second branch 62b is spaced apart to the maximum extent from the first branch 62a and it is possible to hook onto an anatomical structure to be ligated.

When the operator pulls the drive member 35, the convex surface 77 moves towards the side wall 40 and the proximal end portion of the second branch 62b comes to face the orifice 74 of the keeper 71. The ligature element 1 is then in the transport position, and the applicator 30 can be inserted into the cannula. The cross-section of the holder 39 is then no larger than the cross-section of the cylindrical body 31.

In order to open the ligature, the operator pushes back the drive rod 35, then, after hooking onto the anatomical structure, the operator pulls the drive member, in order to bring the second branch 62b closer to the first branch 62a, as shown in FIG. 21. By pulling to a further extent on the drive member 35, the serrated portion of the second branch 62b is caused to penetrate into and to slide in the orifice 74 of the keeper 71, thereby clamping the anatomical structure in the transverse channel of the ligature element 61.

Figure 19:
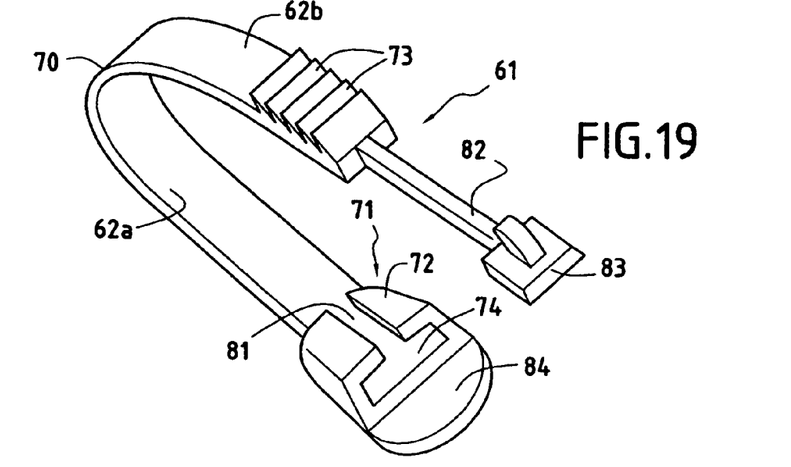
FIG. 19 shows a variant of the second embodiment of the ligature element of the invention.

FIG. 19 shows a variant of the second embodiment of the ligature element 61. This variant differs from the variant shown in FIG. 18 by a longitudinal slot 81 provided in the wall 72 of the keeper 71 and by a tongue 82 situated in alignment with the serrated portion of the second branch 62b. The tongue 82 is of length slightly longer than the length of the keeper 71 and can be inserted into the duct 74 by sliding through the longitudinal slot 81. The tongue 82 is terminated by graspable means 83. The proximal end of the first branch 62a can also have graspable means 84. In which case, the second branch 62b is flexible. In which case, the entire ligature element 61 is made of a flexible material in order to act as a ligature.

Figures 20, 22:
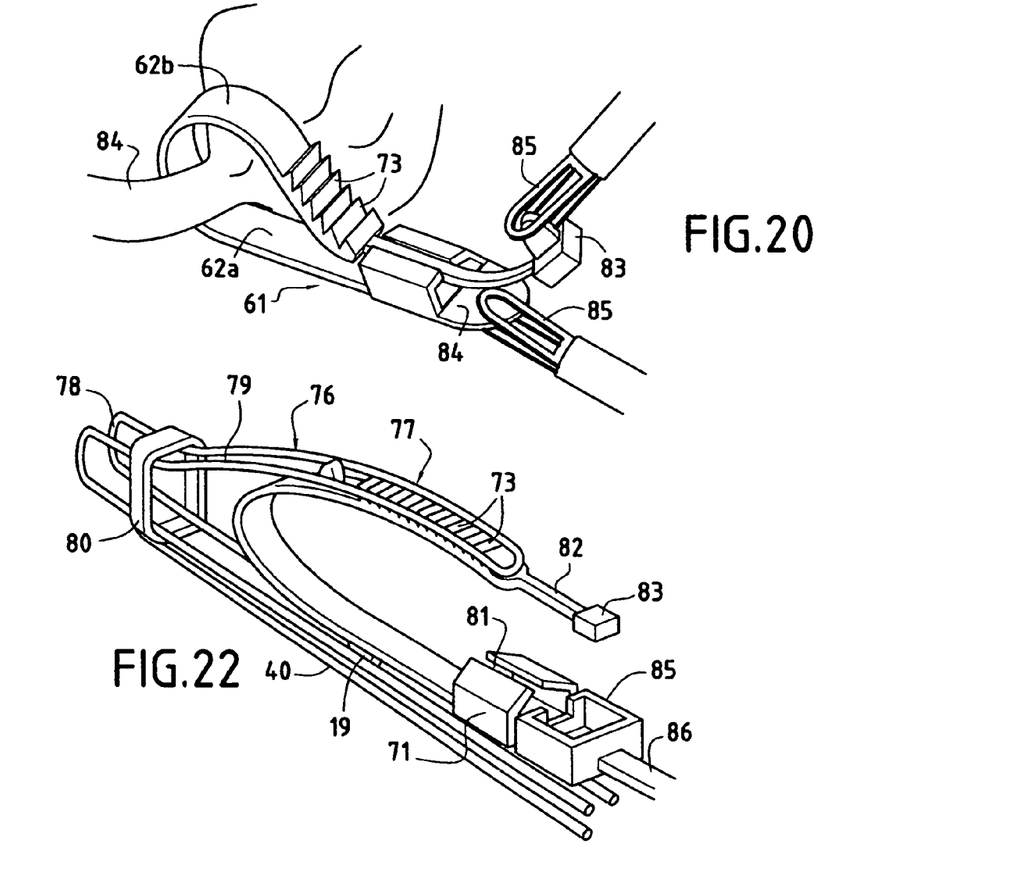
FIG. 20 shows one possible manner of ligating an anatomical structure with the flexible ligature element shown in FIG. 19, without an applicator system, by using standard celioscopic instrumentation.
FIG. 22 is a perspective view showing the distal end of a specific applicator for putting in place a ligature element similar to the ligature element shown in FIG. 19.

FIG. 20 shows one way of mounting the above-described ligature element 61 around the anatomical structure by taking hold of the tongues 84 and 85 by means of celioscopic tweezers.

Said ligature element 61 can also be put in place by means of the above-described applicator 30. When, by axially moving the ring 80, the convex surface 77 is caused to move towards the side wall 40, firstly the tongue 82 passes through the slot 81, and then the serrated portion slides in the duct 74 of the keeper 71.

FIG. 22 shows a variant embodiment of the applicator 30. This applicator 30 has a receptacle 85 in the vicinity of the holder 39 and in which the graspable means 83 situated at the end of the tongue come to be received when the tongue 82 is disposed in the duct 74 of the keeper 71. The receptacle 85 is connected via a second rod 86 to a second drive member (not shown in the drawings) situated at the proximal end of the cylindrical body 31 of the applicator 30.

As can be seen in FIG. 22, the side wall 40 and the spring blade 76 can be implemented in the form of spring wires of circular or flat cross-section. This spring plays an important part: it makes it possible to drive the branch 62b to which it is secured by one or more lugs; its shape at 78 forms a plurality of successive plateaus since, when the ring 80 is pushed towards the end of the instrument, the preformed portion 76 rises, entraining the branch 62b with it, and when the ring 80 is pulled over the bend 79, the portion 76 brings the branch 62b into contact with the keeper 71 and with the receptacle 85. This position is deemed to be the transport position or the position of insertion into an access trocar given that the loop formed by the two branches 62 and 62b is flattened on passing into the trocar and given that the narrow portion 82 is of length determined such that it slides freely in the slot 81 and in the receptacle 85 whose proximal end 85 bis is far enough away to enable the portions 82 and 83 to move. The rectilinear portion 40 of the spring against which a pin 75 slides, receives the lugs 19 that hold the branch 62a and the rear portion of the keeper 71 in the holder. The keeper comes into abutment against a piece in relief 87 on the handle of the applicator so that, when traction is applied to the graspable means 83 by the recessed portion of the receptacle 85, the keeper 71 can remain stationary while the branch 62b and the serrations 73 are pulled through the internal portion of the keeper 71. When the loop formed by the branches 62a and 62b is closed sufficiently onto the anatomical structure to be controlled, the pin 86 is pushed back towards the distal portion of the instrument in order to release the element 61 from its applicator.

Preferably, the ligature element 1 or 61 is pre-mounted on the applicator 30 in the workshop by engaging the lugs 19 into spaces provided for this purpose in the wall of the spring 40 and 76, in order to constitute a sterile assembly ready for use.

A plurality of portions of the applicator 30, and in particular the cylindrical body 31, are made of a plastics material.

The ligature element 1 is put in place by means of the applicator 30 by the operator, under optical video monitoring, thereby making it possible to save having to use an additional trocar and additional tweezers, as is necessary with the current technique.

Figure 23:
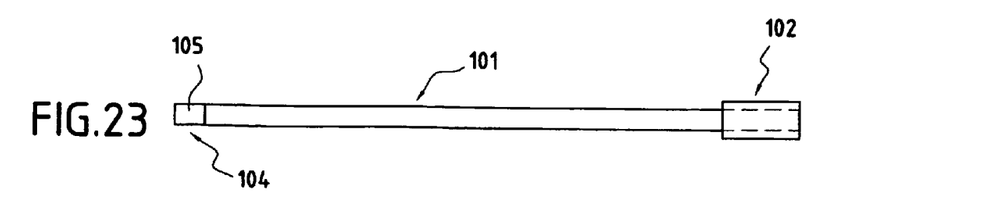
FIG. 23 is a plan view of a third embodiment of the ligature element of the invention.
Figure 24:
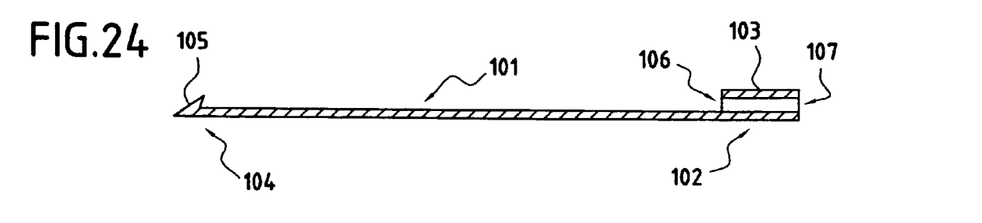
FIG. 24 is a side view of the ligature element of FIG. 23.

FIGS. 23 and 24 show a third embodiment of a ligature element 101 which is in the form of a flexible, relatively long, strip whose proximal end 102 has a keeper 103 on its top or inside face, and whose end of its distal portion 104 has a barb 105 on its top or inside face. The barb 105 serves to be inserted by traction into the keeper 103 via the distal end 106 thereof. By continuing to pull on the barb 105, the distal end 104 is caused to penetrate into and to slide in the keeper 103, and the portion of the strip adjacent to the keeper 103 forms a loop for tightening around the anatomical element to be ligated, it then being possible for the distal portion 104 then to be cut off in front of the proximal end 107 of the keeper 103. The bottom face of the ligature element 101 can, in its middle portion, have serrations that enable it to be locked in the keeper 103 after tightening.

FIGS. 25 to 30 show the applicator 120 used for putting in place the ligature element 101 around an anatomical element 110.

Figure 25:
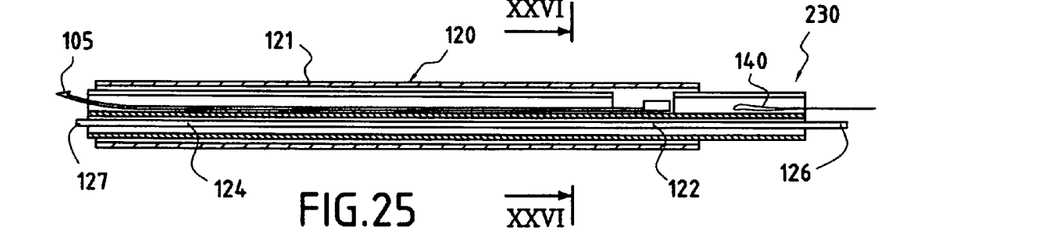
FIG. 25 shows the applicator for putting in place the third embodiment of the ligature element of the invention, prior to the surgical operation.

This applicator 120 essentially comprises a rigid and rectilinear tube 121 whose outside diameter is no larger than 5 mm and whose inside diameter is in the vicinity of 4 mm.

The tube 121 can slidably receive a rectilinear metal rod 122 implemented in the form of a strip having a width in the range 1 mm to 3 mm and a thickness of in the range 4/10 mm to 8/10 mm. At its distal end 123, the rod has a hot-formed spring blade 124 which, in the absence of stress, is in the form of an almost full circle which has a diameter lying in the range five times the inside diameter of the tube 121 and twelve times said inside diameter, and whose cross-section is preferably identical to the cross-section of the rod 122. The diameter of the spring blade 124 is, for example, about 5 cm, and its circumference then lies in the range 15 cm to 20 cm.

The rod 122 and the spring blade 124 are preferably made of the same material and drawn from the same metal strip e.g. made of a Nickel-Titanium alloy, which alloy makes it possible to hot-form springs of circular shape that can resume their initial circular shape after having been retracted or put in an almost rectilinear deployed state in the rigid and rectilinear tube 121.

When the spring blade 124 forms a circle, the circle and the rod 122 lie in the same plane. The spring blade 124 is then in alignment with the rod 122 outside the tube 121, and the junction between the distal portion 123 of the rod 122 and the spring blade 124 is determined so that the axis extending in alignment with the rod 122 intersects the circle in the vicinity of its center 125 and finds itself spaced apart from said center 125 by a distance not greater than two-thirds of the radius of the circle. The external angle formed by the rod 122 and the tangent to the circle at the junction point 123 lies in the range 90° to 180°, for example.

The function of the spring blade 124 is to surround the anatomical structure 110 with the above-described ligature element 101.

Figure 27:
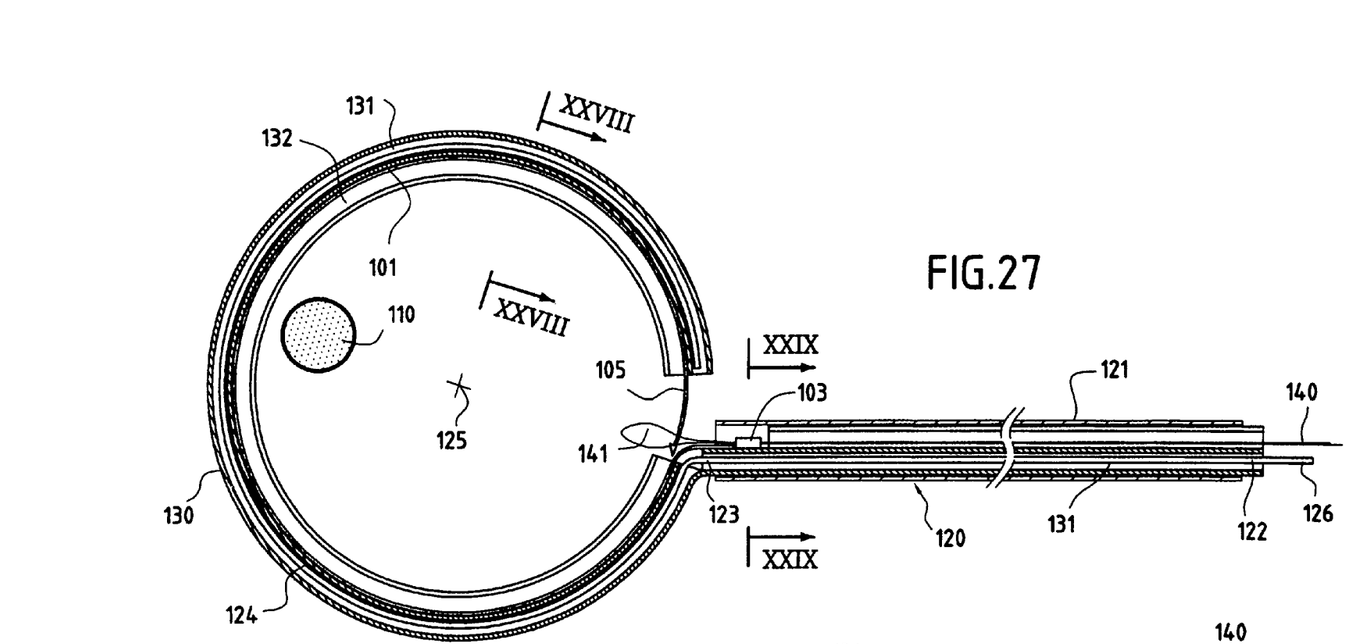
FIG. 27 is a side view of the applicator of FIG. 25, during the surgical operation.
Figure 28:
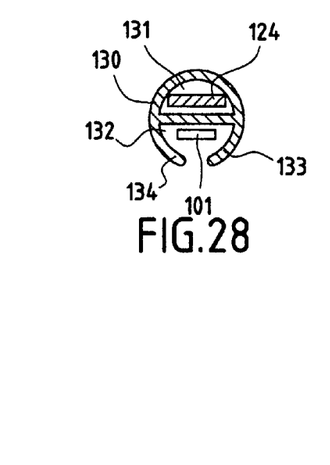
FIG. 28 is a section view of the support of the ligature element on line XXVIII-XXVIII of FIG. 27.
Figure 29:
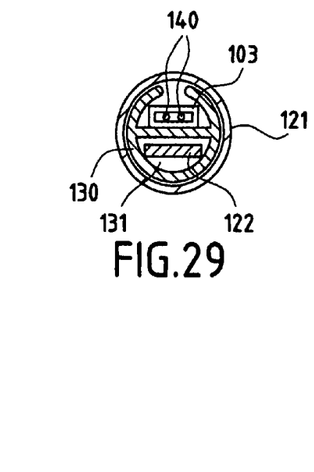
FIG. 29 is a cross-section view of the tube and of the keeper on line XXIX-XXIX of FIG. 27.

To this end, the applicator 120 is also provided with a sheath 130 that is made of a flexible plastics material, that has a smooth surface so that it can slide easily inside the tube 121, and that has a radially outer duct receiving the spring blade 124 and the metal rod 122, and, on the radially inner face of the spring blade 124, a groove 132 in which the ligature element 101 is received, in particular while it is being transported around the anatomical structure 110, as is shown in FIGS. 27 and 28.

Figure 26:
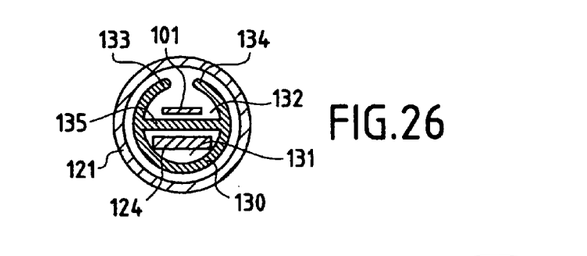
FIG. 26 is a section view of the applicator on line XXVI-XXVI of FIG. 25.

In practice, as can be seen in FIGS. 26 and 28, the sheath 130 is in the form of a tube split over a portion of its length and having an internal partition 135 defining the duct 131 and the guide groove 132.

The guide groove 132 is defined by two lips 133 and 134 and by a wall portion 135 of the duct 131.

The function of the lips 133 and 134 is to retain the longitudinal edges of the ligature element 101, but said lips can move apart in order to release the ligature element 101 while said ligature element is being tightened.

The ligature element 101 is disposed in the guide groove 132 such that the keeper 103 finds itself above the distal end of the metal rod 122, its distal end 104 and in particular the barb 105 finding themselves beyond the free end of the spring blade 124, i.e. below the plane of the rod 122 when the spring blade 124 forms a circle, as is shown in FIG. 27.

The applicator 120 is also equipped with a single or double wire guide or feedthrough 140 which is received in part in the tube 121, which passes through the keeper 103, and which forms a loop or eye 141 beyond the distal end 106 of the keeper 103.

The sheath 130 and the elements 122, 123, and 124 are secured together and the resulting assembly is referenced 230. Although the feedthrough is malleable, it is constrained to move with the assembly 230 when said assembly is pushed.

By exerting traction on the proximal end of the assembly 230, the junction between the rod 122 and the spring blade 124 deforms elastically and penetrates into the tube 121 via its distal end 127. It can be understood that the entire spring blade 124 can be retracted into the tube 121, as is shown in FIG. 25.

Figure 30:
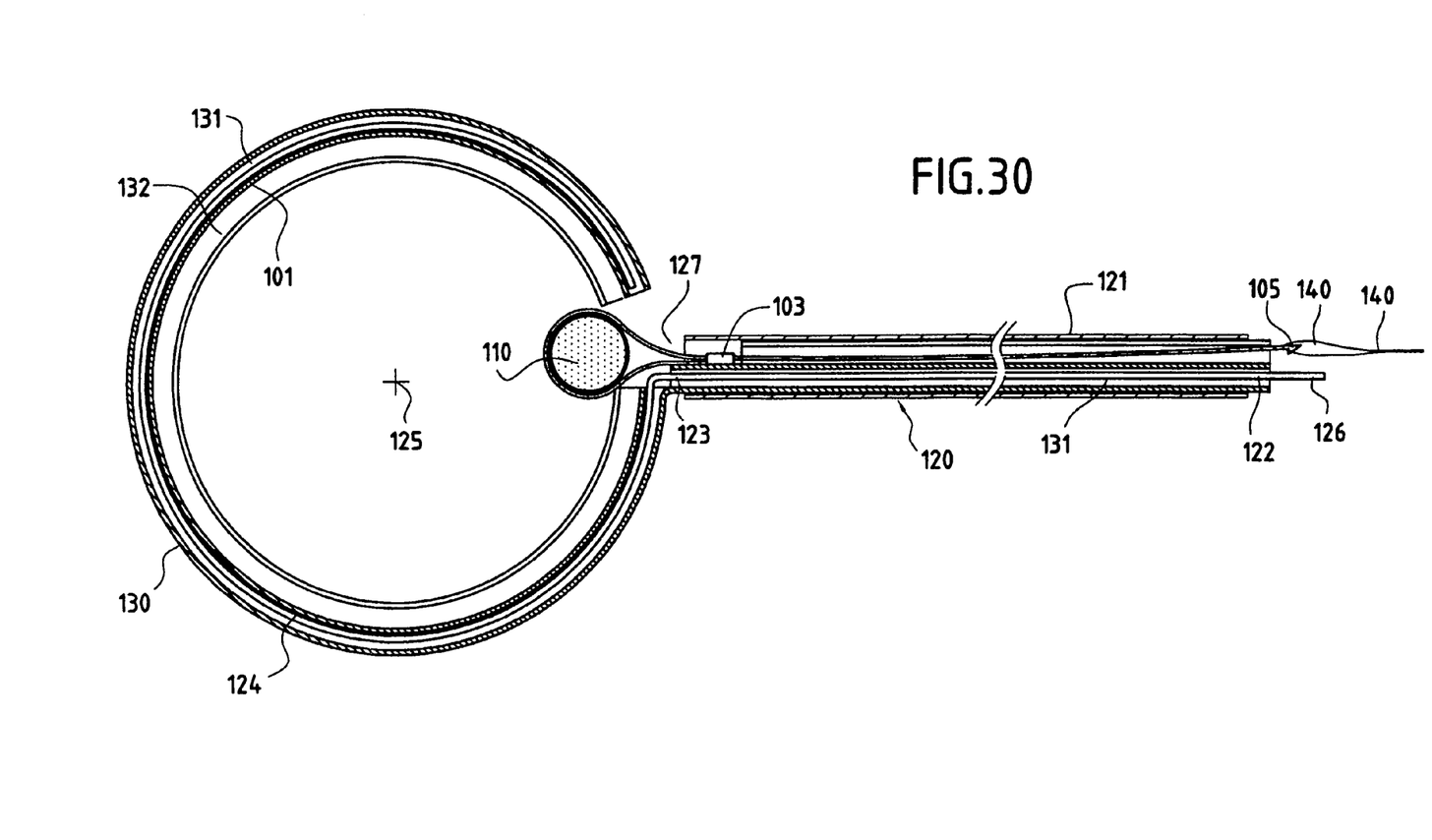
FIG. 30 is a side view of the applicator after the ligature element has been tightened.

As shown in FIG. 27, the barb 105 finds itself under the plane of the loop 141 of the wire feedthrough 140. By exerting traction on the external portion of the feedthrough 140 that projects via the proximal end of the tube 121, the loop 141 co-operates with the barb 105 and makes it possible to pass the barb 105 and the distal portion 104 of the ligature element 101 into the keeper 103 via its distal end 106. While this traction is being exerted, the diameter of the loop formed by the ligature element 101 decreases and the ligature element 101 escapes from the guide groove 132 by the lips 133 and 134 moving apart. Additional traction makes it possible to tighten the ligature element 101 around the anatomical structure 110, as is shown in FIG. 30.

By exerting thrust on the rod 122, the keeper 103 comes out of the tube 121. It is then possible to cut off the distal portion 104 of the ligature element 101 close to the proximal end 107 of the keeper 103.

Figure 31:
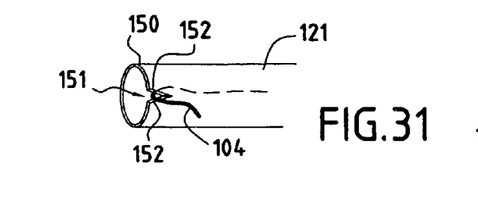
FIG. 31 shows the cutting means for cutting off the distal portion of the ligature element after tightening.

Thus, as shown in FIG. 31, the distal end 150 of the tube 121 is provided with a notch 151 having sharp edges 152 suitable for cutting off the distal portion 104 retained by the feedthrough 140.

Figure 32:
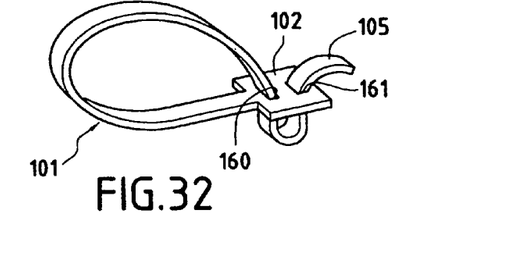
FIG. 32 shows a variant of the third embodiment of the ligature element.

FIG. 32 shows a variant embodiment of the ligature element 101 that differs from the embodiment shown in FIGS. 23 and 24 by the fact that the keeper 103 is replaced by two orifices 160 and 161 provided in the proximal portion 102 and via which the feedthrough 140 passes. By exerting traction on the feedthrough 140, the barb 105 is caused to pass successively through the orifice 160 and then through the orifice 161, thereby, after tightening, guaranteeing that the anatomical structure 110 is ligated.

The invention claimed is:

1. A device for ligating an oblong anatomical structure such as a vermiform appendix or a mesoappendix, or any other vessel or tissue anatomic structures, the device being suitable for being used under celioscopy, said device comprising:

firstly a ligature element in the form of a flexible strip having a proximal portion and a distal portion with a free end, the proximal portion having a keeper, and the distal portion having a barb at its free end and being suitable for being slidably received in said keeper after it has been inserted via the distal end of the keeper after traction has been exerted on the barb; and secondly, an applicator for putting said ligature element in place, said applicator comprising:

a cylindrical tube having a distal end and a proximal end;

a rectilinear metal rod which extends in said tube and which, at its distal end has a spring blade which, in the absence of stress, forms substantially a circle extending from said rod and whose diameter lies in the range five times the inside diameter of said tube to twelve times said inside diameter, said blade being suitable for being received in said tube in the deployed state and for resuming its circular shape when it is brought out via the distal end of said tube;

a sheath having a radial outer duct in which the spring blade is received, and a radial inner guide groove in which the ligature element is received, said inner guide groove being defined by two lips configured for retaining, at least while it is being transported, the ligature element along an inside face of the spring blade, and for releasing the ligature element while it is being tightened; and a feedthrough passing through said keeper and, at the front of distal end of said keeper, forming an eye into which the distal end of the ligature element is inserted when the spring blade forms a circle, so that traction exerted on said feedthrough causes said eye to be hooked by the barb, causes the distal portion of the ligature element to be inserted into said keeper, and causes said ligature element to be tightened.

2. A device according to claim 1, wherein the lips move apart to release said ligature element while it is being tightened.

3. A device according to claim 1, wherein the keeper is constituted by two orifices provided in the proximal portion of the ligature element and via which the feedthrough passes.

4. A device according to claim 1, wherein the distal end of the tube is also provided with cutting means for cutting off the distal end of the ligature element after said ligature element has been tightened.

5. A device according to claim 4, wherein the cutting means are formed by the sharp edges of a notch provided at the distal end of the tube.

* * * * *